(12) United States Patent
von Gutfeld et al.

(10) Patent No.: US 6,230,038 B1
(45) Date of Patent: May 8, 2001

(54) IMAGING OF INTERNAL STRUCTURES OF LIVING BODIES BY SENSING IMPLANTED MAGNETIC DEVICES

(75) Inventors: Robert Jacob von Gutfeld, New York; James Francis Ziegler, Yorktown Heights, both of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/241,506

(22) Filed: Feb. 1, 1999

(51) Int. Cl.$^7$ .................................................. A61B 19/00
(52) U.S. Cl. ........................ 600/409; 600/424; 128/899
(58) Field of Search ........................... 600/407, 409, 600/424; 128/899; 324/207.11, 207.13, 207.17, 207.22, 214, 207.26, 219

(56) References Cited

U.S. PATENT DOCUMENTS

| | | | |
|---|---|---|---|
| 4,173,228 | * 11/1979 | Van Steenwyk et al. | 600/409 |
| 4,317,078 | * 2/1982 | Weed et al. | 600/424 |
| 4,905,698 | * 3/1990 | Strohl, Jr. et al. | 600/424 |
| 5,494,035 | * 2/1996 | Leuthold et al. | 600/409 |
| 5,558,091 | * 9/1996 | Acker et al. | 128/899 |
| 5,645,065 | * 7/1997 | Shapiro et al. | 128/899 |
| 5,664,582 | * 9/1997 | Szymaitis | 128/899 |
| 5,729,129 | * 3/1998 | Acker | 600/424 |
| 5,752,513 | * 5/1998 | Acker et al. | 128/899 |
| 5,758,667 | * 6/1998 | Slettenmark | 128/899 |
| 5,762,064 | * 6/1998 | Polvani | 128/899 |
| 5,865,744 | * 2/1999 | Lemelson | 600/407 |
| 5,879,297 | * 3/1999 | Haynor et al. | 600/424 |
| 5,882,304 | * 3/1999 | Ehnholm et al. | 600/424 |
| 5,902,238 | * 5/1999 | Golden et al. | 600/424 |
| 5,954,647 | * 9/1999 | Bova et al. | 600/407 |
| 6,014,580 | * 1/2000 | Blume et al. | 600/424 |
| 6,052,610 | * 4/2000 | Koch | 600/424 |
| 6,073,043 | * 6/2000 | Schneider | 600/424 |

* cited by examiner

Primary Examiner—Teresa Walberg
Assistant Examiner—Fadi H. Dahbour
(74) Attorney, Agent, or Firm—Casey P. August

(57) ABSTRACT

The invention provides a system for therapeutic treatment of an organ, tumor, or other internal structure of a living body with therapeutic radiation after implantation, at the organ, of a magnetic element to identify the location of the organ, the element being capable of emitting a magnetic signal in response to an applied magnetic field. The system comprises a magnetic field generator for irradiating the magnetic element with an applied magnetic field, a movable magnetic field sensor for detecting the magnetic signal from a plurality of selected mutually displaced positions to produce a corresponding plurality of element-locating signals, a computing apparatus for converting the signals to a location image of the internal structure, and a controlled source of therapeutic radiation for focussing a selected degree and duration of therapeutic radiation at a target determined from the location image of the magnetic element. Preferably, the magnetic element is a length of wire of an amorphous magnetic material which produces a magnetic signal that exhibits non-linear Bark+hausen jumps in response to an applied ac magnetic field.

47 Claims, 4 Drawing Sheets

IMAGING OF INTERNAL STRUCTURES OF LIVING BODIES BY SENSING IMPLANTED MAGNETIC DEVICES

CROSS-REFERENCE TO RELATED APPLICATIONS

This application is related to application Ser. No. 09/241,503, entitled "FOCUSSING OF THERAPEUTIC RADIATION ON INTERNAL STRUCTURES OF LIVING BODIES", filed on the same date herewith, by James F. Ziegler and Robert J. von Gutfeld, which application is incorporated herein by reference.

FIELD OF THE INVENTION

The present invention relates to the treatment of organs, tumors, and other internal structures of living bodies with therapeutic radiation, and to methods and systems adapted to the location and therapeutic treatment of such internal structures by the use of implanted magnetic elements and magnetic fields.

BACKGROUND OF THE INVENTION

There are numerous examples where specific hidden positions within items, animals or humans need to be determined with accuracy. For example, It is generally acknowledged by oncologists that directing a source of radiation accurately at an internal tumor (e.g. carcinoma) for treatment is difficult because the precise location of the tumor is elusive. As a result, substantial amounts of radiation frequently miss the intended target, i.e. the tumor or unwanted cellular growth. This leads to the danger of radiating healthy body tissue, giving rise to tissue damage and extensive bleeding, at times from vital organs in the vicinity of the tumor.

Under the best of circumstances, preparation for radiation treatment includes obtaining tomographic images of the tumor and surrounding tissue, typically recorded several days prior to the onset of radiation treatment. The 3-D reconstruction of the images results in accurately locating the tumor in relation to the body as a whole. However, since radiation treatment may occur over a matter of months, there can be considerable shifts or displacements of the organ-containing tumor from the position originally determined from the tomograph. As a result, relying on the original tomographic positioning data can result in the radiation beam missing the target (tumor or other internal structure) either partially or even completely, striking instead regions not meant to be irradiated.

OBJECTS OF THE INVENTION

Several novel methods are presented for determining the position of remotely located regions not visible to the eye. The main emphasis of the invention is to improve the ability to accurately direct radiation onto tumors or unwanted cell growths by certain magnetic markers.

Since these positions are visually imperceptible it is proposed here to embed some type of locator such as a transmitter or the like that can emit an energy field which is detectable externally. From the amplitude and angular dependence of the detected signal as a function of position, it is then possible to deduce the precise location of the magnetic element. Such position determinations are especially important in the field of oncology where precise location of a tumor or other internal structure of a living body needs to be known prior to administering radiation treatment.

This application proposes the use of specially shaped high permeability, preferably non-linear magnetic materials that can serve as remotely positioned locators. Typically these materials are embedded in a living body and out of visual contact. Exposure to a low frequency ac magnetic field causes the radiation of non-linear magnetic fields to emanate from the magnetic material which can be detected by one or more externally located pickup coils or other magnetic sensors. A frequency analyzer may be used to examine one or more higher harmonics emitted by non-linear magnetic material Fields from ferrous solids can also be mapped in an externally applied dc field as can permanently magnetized objects without the application of an externally applied field. If the material has a sharp Barkhausen jump as is the case for certain amorphous magnetic wires (produced for example by the Unitika Corporation, of Hyogo, Japan), flux re-entrant reversals occur in the presence of a small applied ac field. These sudden magnetic reversals give rise to voltage spikes when sensed by a pickup coil. Filtering of the ac field in the sensing circuit makes it possible to map these pulses as a function of position enabling the determination of the wire's location.

While the present invention has other applications, the preferred embodiments relate to medical applications, specifically, locating tumors for radiation treatment. Small amounts of magnetic material in the form of spheres or short lengths of amorphous wire are first implanted in or near the tumor. Once location of the implant is determined by way of the magnetic field mapping, that is magnetic amplitude as a function of position, the radiation beam can be directed precisely to the target area.

SUMMARY OF THE INVENTION

The present invention broadly provides a method of determining the location of an internal structure of a living body comprising the steps of:

a) implanting, at the aforesaid internal structure, an element comprising a magnetic material to identify a selected location of the internal structure, the element being capable of emitting a magnetic signal in response to an applied magnetic field, b) irradiating the element with an applied magnetic field, c) detecting the magnetic signal from a plurality of selected mutually displaced positions to produce a corresponding plurality of element-locating signals, and d) converting the element-locating signals to a location image of the internal structure.

For the purpose of therapeutic treatment of a tumor or other internal structure, the method includes a further step of e) focussing a selected degree and duration of therapeutic radiation at a target determined from the aforesaid location image of the aforesaid element.

The present invention further provides a system for determining the location of a tumor or other internal structure of a living body after implantation, at the aforesaid internal structure, of an element comprising a magnetic material to identify a selected location of the internal structure, the element being capable of emitting a magnetic signal in response to an applied magnetic field. The inventive system comprises: a) a magnetic field generator for irradiating the aforesaid element with an applied magnetic field, b) a movable magnetic field sensor for detecting the aforesaid magnetic signal from a plurality of selected mutually displaced positions to produce a corresponding plurality of element-locating signals, and c) a computing apparatus for converting these signals to a location image of aforesaid tumor or other internal structure.

For the the purpose of therapeutic treatment of a tumor or other internal structure, the system further comprises d) a controlled source of therapeutic radiation for focussing a selected degree and duration of therapeutic radiation at a target determined from the aforesaid location image of the aforesaid element.

According to a preferred embodiment of the invention, the applied magnetic field is spatially and temporally uniform, sometimes called a "dc" field.

Alternatively, applied magnetic field may be a low frequency ac (e.g. 60 Hz) magnetic field and the magnetic signal is non-linear in response to this low frequency ac magnetic field.

According to a preferred embodiment, the applied magnetic field is an ac field and the element comprises an amorphous magnetic material, said magnetic signal being characterized by non-linear Barkhausen jumps in response to this applied ac magnetic field.

Preferably, the embedded element is coated with absorbing material which absorbs therapeutic radiation (e.g. lead) and is pervious to magnetic fields. The element may last be coated with a biologically inert material (e.g. PMMA, or polymethyl methacrylate) to prevent injury to the living body in which the element is to be embedded.

According to another preferred embodiment of the invention, the aforesaid embedded element may comprise a permanently magnetized material. For this embodiment, the method of determining the location of an internal structure (e.g. tumor) of a living body comprises the steps of:

a) implanting, at the aforesaid internal structure, an element comprising a permanently magnetized material to identify a selected location of the aforesaid internal structure, this element being capable of emitting a magnetic signal, b) detecting the aforesaid magnetic signal from a plurality of selected mutually displaced positions to produce a corresponding plurality of element-locating signals, and c) converting these element-locating signals to a location image of the aforesaid internal structure.

For the purpose of therapeutic treatment of a tumor or other internal structure, the method further comprises d) focussing a selected degree and duration of therapeutic radiation at a target determined from the aforesaid location image of said element.

Corresponding to this preferred embodiment, the invention provides a system for determining the location of an internal structure (e.g. tumor) of a living body after implantation, at the aforesaid internal structure, of an element comprising a permanently magnetized material to identify a selected location of this internal structure, the permanently magnetized element being capable of emitting a magnetic signal. This system comprises:

a) a movable magnetic field sensor for detecting the aforesaid magnetic signal from a plurality of selected mutually displaced positions to produce a corresponding plurality of element-locating signals, and b) a computing apparatus for converting the element-locating signals to a location image of the internal structure.

For the the purpose of therapeutic treatment of a tumor or other internal structure, the system comprises c) a controlled source of therapeutic radiation for focussing a selected degree and duration of therapeutic radiation at a target determined from the aforesaid location image of the permanently magnetized element.

Two geometries of two types of magnetic elements are described here which can be embedded in a living body by surgical or orthoscopic means to accurately locating internal tumors for radiation treatment. The embedded magnetic element is of a known geometrical shape. It can be in the form of a permanently magnetized or a non-magnetized ferrous material, whose field is mapped as a function of position. An ac or dc magnetic field may be used to query the field of the ferrous object element. Two preferred geometries of this invention are: 1) a small homogeneous ferrous sphere of known radius, preferably with a non-linear permeability and 2) a highly permeable amorphous magnetic wire of known length. It should be obvious to those skilled in the art that other magnetic geometries could also be used.

BRIEF DESCRIPTION OF THE DRAWINGS

FIG. 1$b$ is a schematic cross-sectional view of a permanently magnetized sphere and the external radial field $H_r$ for a fixed direction of magnetization M.

FIG. 1$c$ shows a graph of a typical hysteresis curve for the magnetic sphere of FIGS. 1$a$ and $b$.

FIG. 3$b$ is a graph of the absolute value of voltage induced in the pickup coil of FIG. 3$a$ as a function of its position along the length of the amorphous magnetic wire.

FIG. 3$c$ is a graph of the applied voltage and the voltage pulse $V_s$ induced in the pickup coil of FIG. 3$a$ as a function of time, at a selected perpendicular distance from the magnetic wire.

FIG. 3$d$ is a schematic view showing the field lines emanating from an amorphous magnetic wire when placed in an applied ac magnetic field.

FIG. 4$b$ is a schematic view of a syringe injecting the encapsulated wire of FIG. 4$a$ into a tumor or other internal structure to be irradiated.

DETAILED DESCRIPTION OF THE INVENTION

Figure 1A:
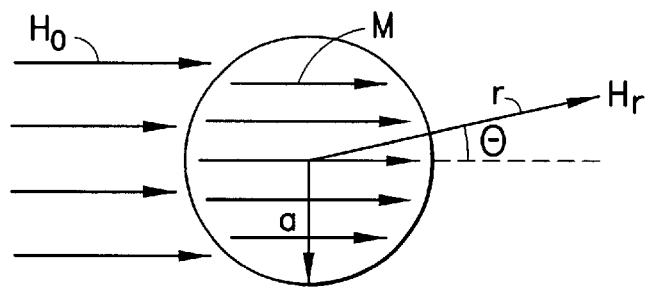
FIG. 1$a$ is a schematic cross-sectional view of a sphere of highly permeable magnetic material placed in a spatially uniform dc magnetic field and the resulting direction of magnetization, M, and the radial magnetic field dependence $H_r$.

In general, non-linear magnetic materials produce a unique magnetic signature usually rich in harmonics when in the presence of an externally applied sinusoidal magnetic field. The field from the magnetic material can be readily sensed by a pickup coil or other magnetic sensors such as Hall probes as well as a variety of magnetometers. The field from a non-linear material in the presence of an applied ac field can be frequency analyzed and any one of the several harmonics can be chosen to measure the emitted field as a function of position. In fact, fields from a sensor element of magnetic material in either an ac or dc field can be mapped as a function of position so that for certain simple geometries the location of the magnetic element can be determined simply and precisely. It thus becomes possible to locate elements of such magnetic material when they are hidden or out of view so that they can serve as locators when interrogated by an applied ac or dc magnetic field or even without an external applied magnetic field when the elements are permanent magnets.

While magnetic material of various geometries and permeabilities can be useful to serve as position locators or elements, the present invention specifically describes two particular preferred embodiments and geometries, namely ferrous magnetic spheres and amorphous highly permeable magnetostrictive wires. These two forms of magnetic element are chosen because when magnetically interrogated, their resultant fields as a function of position are relatively simple to calculate. Therefore, the measured fields can be readily interpreted for pinpointing the position of the hidden element. While this type of 'blind' locating is quite generic as is easily recognized by those skilled in the art, in this invention we describe preferred embodiments which relate to the field of oncology. The magnetic material is embedded onto or in close proximity of tumors or unwanted cell growths which are to be treated by therapeutic radiation therapy. The reason for the embedded locator is that radiation treatment often takes place in numerous steps or "fractions" over a period of months during which time the tumor, organ containing the tumor, or other internal structure can move with respect to the initial position determined by CAT (computer aided tomography) scan or MRI (magnetic resonance imaging). As a result of this shift, the radiation often misses the intended target and exposes healthy tissue to damaging doses of radiation.

The present invention specifically describes the use of ferrous magnetic spheres or amorphous magnetic wire with large Barkhausen jumps as locator elements whose fields are mapped to determine the magnetic materials' location. The location is then used to direct radiation for treatment in the vicinity of the magnetic material. Other magnetic geometries can also be used for field mapping and locating but may not be as convenient as these two preferred embodiments.

EXAMPLE I

Ferrous Magnetic Sphere

Figure 1B:
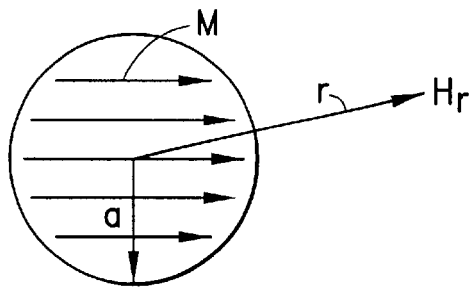
Figure 1C:
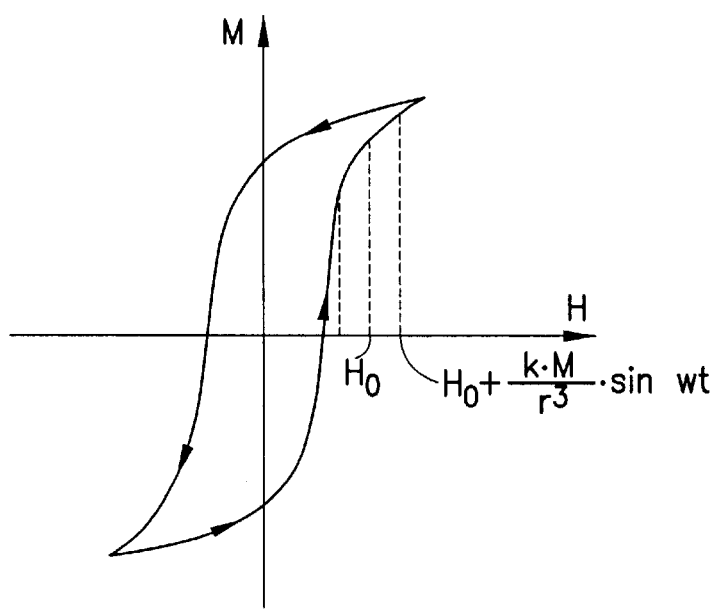

FIG. 1$a$ shows the magnetization, M, within a sphere of ferrous magnetic material and the external field $H_r$ produced when a high permeability magnetic sphere of radius "a" is in the presence of a uniform dc magnetic field $H_0$, where r is the distance from the sphere's center and θ is the azimuthal angle with respect to the applied field direction. An ac external field can also be used but may be not as practical. It can be shown (see for example B. I. Bleaney and B. Bleaney, Electricity and Magnetism Chp IV, Oxford University Press, 1989) that the radial field $H_r$ from the sphere in a dc uniform magnetic field falls off as $M(r^{-3})\cos θ$, where r is the distance from the center of the sphere of radius "a" to the position of measurement, where M is the magnetization of the sphere.

A similar field dependence is true for a magnetized (pre-magnetized) sphere without an externally applied field, as shown in FIG. 1$b$, where $H_r$ varies as $a^3 M(r^{-3})$.

Furthermore, the resulting field is proportional to the magnetization, M, of the sphere which in turn is a function of the applied field. In a sinusoidally applied field, the value of M will vary non-linearly such that the sphere emits a time varying field containing harmonics, readily sensed by a pickup coil or other magnetic sensors. When the magnetic signal is filtered to suppress the fundamental, the sphere's harmonic field can be mapped as a function of position.

To obtain the largest non-linearity, it is best to operate in the non-linear portion of the H-M hysteresis curve shown in FIG. 1$c$, where a dc bias field $H_0$ can be used to access the most non-linear region and a small ac field, such as kM(r$^-$3)sin wt is superimposed to produce the maximum harmonic content. FIG. 1$c$ shows a typical hysteresis curve for the magnetic materials of FIGS. 1$a$ and 1$b$.

Figure 2:
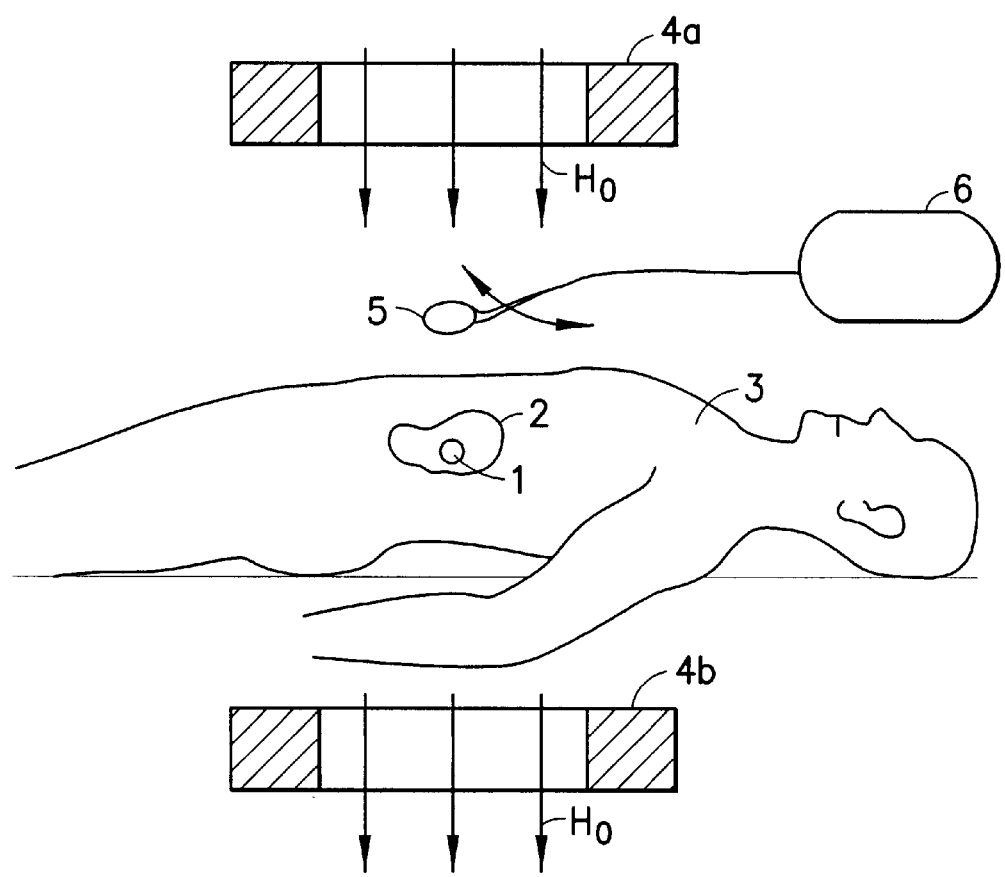
FIG. 2 is a schematic view of a magnetic sphere embedded in or near a tumor or other internal structure together with an applied magnetic field, a movable magnetic sensor such as a coil, Hall probe or magnetometer, and a computing apparatus for calculating a location image of the tumor.

In order to determine the position of a sensor element 1 such as a non-magnetized ferrous sphere, it is surgically or orthoscopically embedded at a selected location (e.g. center) in a tumor or other internal structure 2 of a patient's body 3, as shown in FIG. 2. The patient is placed in a dc (spatially and temporally uniform) uniform magnetic field $H_0$ such as that produced by a magnetic field generator represented by a pair of Helmholtz coils 4$a$, 4$b$ driven by a dc current. The magnetization of the sphere 1 will be in the same direction as the applied field $H_0$. When the applied field $H_0$ is removed, the ferrous sphere 1 stays magnetized at or near its remanent value.

Thus a permanent magnetic field direction is established. The strength of this field can be mapped externally using a magnetometer or Hall probe as a movable magnetic field sensor 5. To determine the exact location of the sphere 1, it is necessary to first seek the maximum field and then measures the field at a small azimuthal angle θ (not shown) to either side of the maximum. When the field falls off as the cos θ to either side of the maximum, the direct line of sight to the sphere 1 has been located. This then is the ray along which the therapeutic radiation beam (not shown) should be directed with the aid of a coordinating computing apparatus 6.

An ac field rather than the dc field can also be applied by the Helmholtz coils, but this will have limited application due to skin depth effects in the ferrous material of element 1. When an ac field is used, a sensor coil 5 can be used to pick up the magnetic signal and if sufficiently non-linear, the applied signal can be filtered leaving only the harmonics from the sphere.

Mapping of either the dc or ac fields which emanate from the ferrous sphere as a function of position can be done in order to locate the embedded magnetic element 1. The above forms of mapping can be done prior to each radiation treatment to assure that the radiation is reaching the intended internal structure 2. After treatment is completed, the element 1 may be removed or left in place, depending on medical determination.

EXAMPLE II

Amorphous Magnetostrictive Wire

There are certain types of magnetic wire produced for example by the Unitika Corp. of Japan that are magnetically very anisotropic and have an unusual domain pattern such that for a very small applied ac field (peak field less than 1 Oersted) depending on the length and diameter of the wire, there is an abrupt switching or reversal of the core (longitudinal) magnetic domains. This type of sudden magnetic field switching at a fixed value of applied field is known as the Barkhausen effect and produces a high frequency signal which has been observed in certain ferrous bulk materials for some time. In order to make use of this effect in the present context, it is essential to use an ac field so that a magnetic sensing element will experience a large flux change in a short increment of time. The emitted magnetic pulse is generally so short in duration that its frequency components are much higher than the applied ac field which is generally on the order of 1 kHz or less, preferably less than 200 Hz.

Figure 3A:
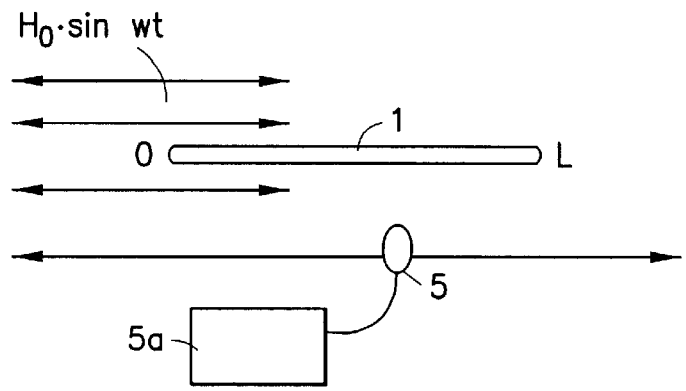
FIG. 3$a$ is a schematic view of an amorphous magnetic wire of length L being scanned by a magnetic field sensor, which includes a pickup coil and a voltage measuring device, while the wire is being irradiated by an applied ac magnetic field.
Figure 3B:
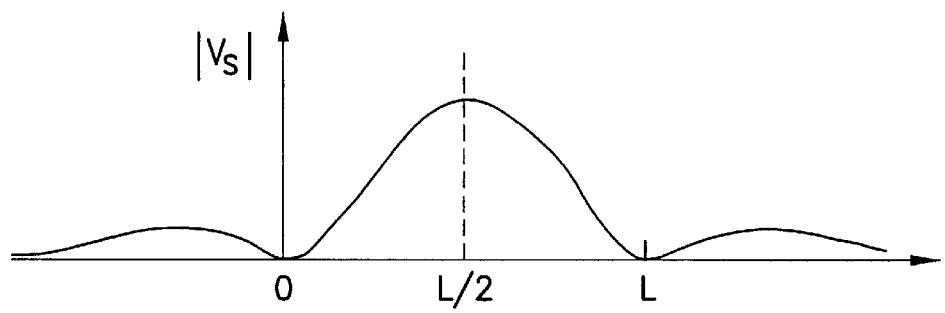

A typical wire 1 of length L is shown in FIG. 3a being scanned along its length by a magnetic field sensor comprising pickup coil 5 and voltmeter 5a and the absolute value of the corresponding temporal voltage pulse $V_s$ due to Barkhausen switching is shown in FIG. 3b. Since the wire is extremely anisotropic (so that the applied field $H_0$ sin wt generally lies in the direction of the wire's axis) it is possible to map the Barkhausen jump field $V_s$ (which occurs at a fixed value $H_s$ of applied field in FIG. 3c) without a frequency analyzer by simply filtering out the applied field as before, e.g. using a notch filter or a high frequency band pass filter. Furthermore, due to the wire's anisotropy, the direction of the applied ac field is not critical with respect to the axis of the wire.

Figure 3C:
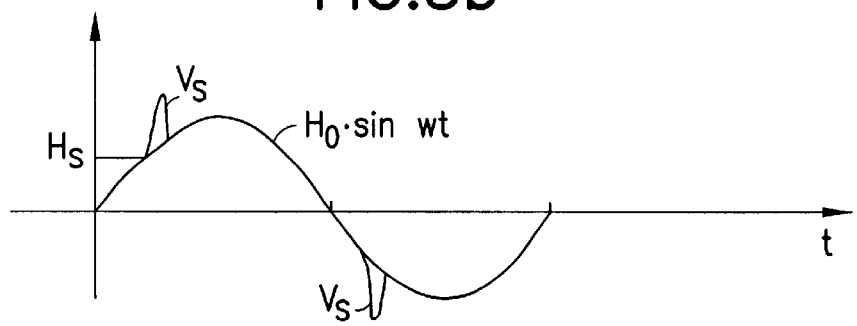

Field mapping can be accomplished using a coil 5 that is oriented in a plane essentially normal to the axis of wire 1, as in FIG. 3a. In that position, the coil 5 will pick up a maximum signal, as in FIG. 3b, at the midpoint of the wire 1 due to the magnetic field lines of the wire as shown in FIG. 3c. Away from the wire's axis, the emitted field from the wire rapidly goes to zero.

Figure 3D:
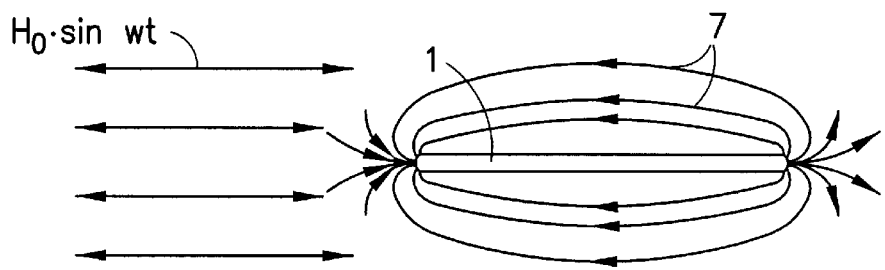

Alternatively, the wire's field can be mapped using a sensing coil, Hall probe or magnetometer whose plane is parallel to the axis of the wire. Here, the maximum Barkhausen field will be sensed at the ends of the wire so that the midpoint of the wire is easily determined. Again, this is due to the field lines of the wire, as shown in FIG. 3d, where the ends of the wire have a maximum number of flux lines that are approximately perpendicular to the axis of the wire and therefore couple into the plane of the sensor.

Figure 4A:
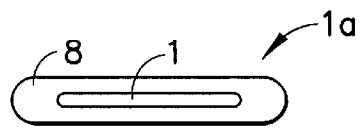
FIG. 4$a$ shows a coated amorphous magnetic wire encapsulated in a non-magnetic, biologically inert casing.
Figure 4B:
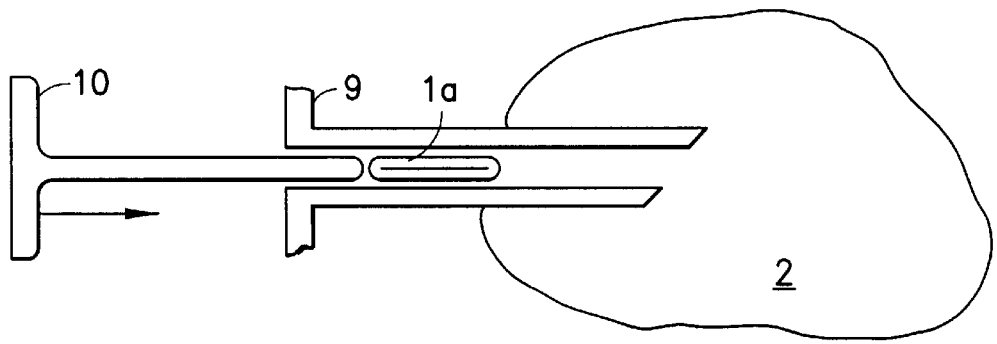

To embed the wire element, it is desirable to first encapsulate the wire 1 with a biologically inert coating 8 to form a small, biologically inert ampule (or capsule) 1a as shown in FIG. 4a that can be surgically implanted or even injected into tumor 2 using a large bore needle 9 and syringe 10, as shown in FIG. 4b. Further, to prevent any damage to the wire element 1 from radiation, the wire or the interior surface of the ampule 1a can first be coated with a radiation absorbing material (such as lead, not shown) which will not interfere with magnetic fields.

Figure 5:
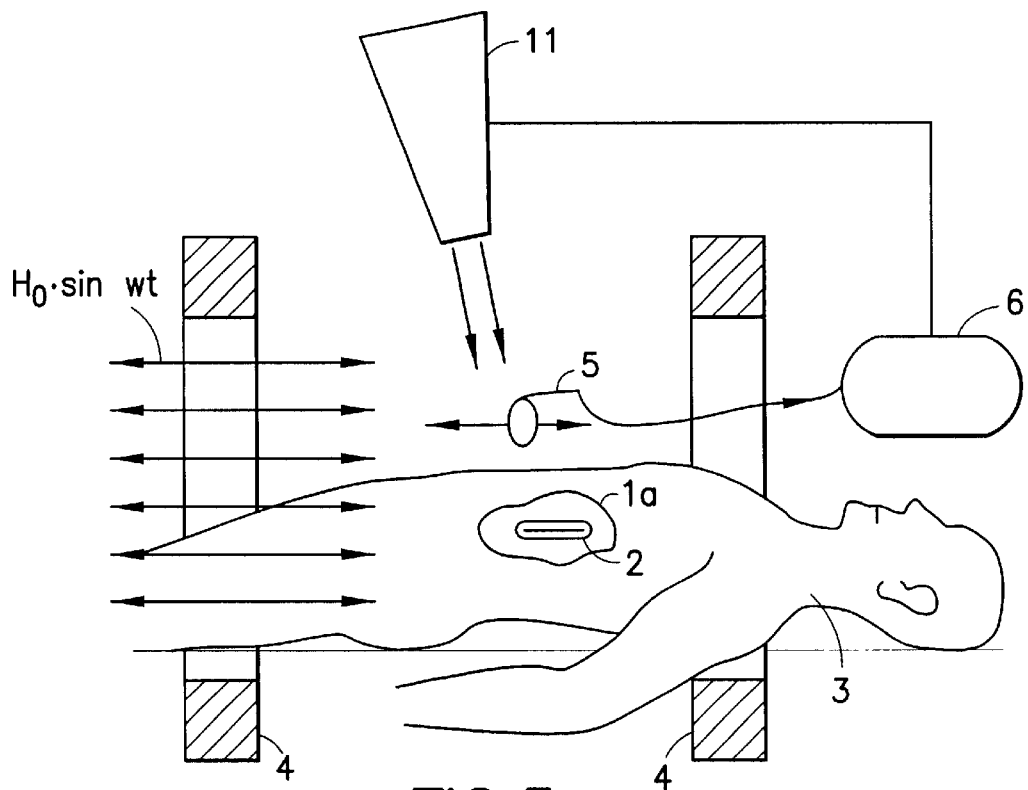
FIG. 5 shows a system for therapeutic treatment of tumors utilizing an embedded amorphous magnetic wire element, in accordance with the present invention.

FIG. 5 shows a novel therapeutic treatment system for treating a tumor or other internal structure 2 of a living body 3 where at least one magnetic element 1 has been implanted surgically or laproscopically at the center or other selected location of tumor 2. As shown in FIG. 5, element 1 is a capsule 1a (as in FIG. 4a) containing an amorphous magnetic wire. Body 3 is positioned for irradiation by an ac applied magnetic field $H_0$ sin(wt) produced by a magnetic field generator formed by a pair of Helmholtz coils 4. A movable magnetic field sensor 5 is movable over a number of mutually displaced (e.g. raster scanned) positions to pick up magnetic Barkhausen jump signals from element 1 and transmit them as electrical voltage signals of varying amplitude to computing apparatus 6. The voltage signals are converted by computing apparatus 6 to a location image of tumor 2. The computing apparatus 6 then signals the controlled source 11 of therapeutic radiation to cause the latter to focus its radiation at a target determined from the location image of tumor 2.

While FIGS. 2 and 5 show use of only a single element to help locate a tumor, it should be understood that a plurality of elements 1 can be implanted, for example in a central circle or at the periphery of the tumor. In that arrangement, a maximum signal would be detected over the center of the configuration of locator elements 1.

While the present invention has been described with reference to preferred embodiments in order to facilitate a better understanding of the invention, those skilled in the art will recognize that the invention can be embodied in various ways without departing from the scope and spirit of the invention as set forth in the appended claims.

What is claimed is:

1. A method of determining the location of an internal structure of a living body comprising the steps of:
   a) implanting, at said internal structure, an element comprising a magnetic material to identify a selected location of said internal structure, said element being capable of emitting a magnetic signal in response to an applied magnetic field,
   b) irradiating said element with an applied magnetic field,
   c) detecting said magnetic signal from a plurality of selected mutually displaced positions to produce a corresponding plurality of element-locating signals, and
   d) converting said element-locating signals to a location image of said internal structure.

2. A method as set forth in claim 1, where said applied magnetic field is spatially and temporally uniform.

3. A method as set forth in claim 1, said applied magnetic field being a low frequency ac magnetic field.

4. A method as set forth in claim 3, wherein said magnetic signal is non-linear in response to said low frequency ac magnetic field.

5. A method as set forth in claim 1, wherein said applied magnetic field is an ac field and said element comprises an amorphous magnetic material, said magnetic signal being characterized by Barkhausen jumps in response to an applied ac magnetic field.

6. A method as set forth in claim 5, wherein said element is elongated in form.

7. A method as set forth in claim 6, wherein said element is a length of wire comprising an amorphous magnetic material.

8. A method as set forth in claim 7, wherein said element is coated with absorbing material which absorbs therapeutic radiation and is pervious to magnetic fields.

9. A method as set forth in claim 1, wherein said applied magnetic field is an ac field and said element comprises an amorphous magnetic material, said magnetic signal being characterized by non-linear Barkhausen jumps in response to an applied ac magnetic field.

10. A method as set forth in claim 9, wherein said element is spheroidal in form.

11. A method as set forth in claim 1, wherein said applied magnetic field is a dc field and said element comprises a ferromagnetic material.

12. A method as set forth in claim 1, wherein said location image is a target for focussing therapeutic radiation thereon.

13. A method of therapeutic treatment of an internal structure of a living body with therapeutic radiation, comprising the steps of:
   a) implanting, at said internal structure, an element comprising a magnetic material to identify a selected location of said internal structure, said element being capable of emitting a magnetic signal in response to an applied magnetic field,
   b) irradiating said element with an applied magnetic field,
   c) detecting said magnetic signal from a plurality of selected mutually displaced positions to produce a corresponding plurality of element-locating signals,
   d) converting said element-locating signals to a location image of said structure, and
   e) focussing a selected degree and duration of therapeutic radiation at a target determined from said location image of said internal structure.

14. A method as set forth in claim 13, where said applied magnetic field is spatially and temporally uniform.

15. A method as set forth in claim 13, said applied magnetic field being a low frequency ac magnetic field.

16. A method as set forth in claim 15, wherein said magnetic signal is non-linear in response to said low frequency ac magnetic field.

17. A method as set forth in claim 13, wherein said applied magnetic field is an ac field and said element comprises an amorphous magnetic material, said magnetic signal being characterized by Barkhausen jumps in response to an applied ac magnetic field.

18. A method as set forth in claim 17, wherein said element is elongated in form.

19. A method as set forth in claim 18, wherein said element is a length of wire comprising an amorphous magnetic material.

20. A method as set forth in claim 19, wherein said element is coated with absorbing material which absorbs therapeutic radiation and is pervious to magnetic fields.

21. A method as set forth in claim 13, wherein said applied magnetic field is an ac field and said element comprises an amorphous magnetic material, said magnetic signal being characterized by non-linear Barkhausen jumps in response to an applied ac magnetic field.

22. A method as set forth in claim 21, wherein said element is spheroidal in form.

23. A method as set forth in claim 13, wherein said applied magnetic field is a dc field and said element comprises a ferromagnetic material.

24. A system for determining the location of an internal structure of a living body after implantation, at said internal structure, of an element comprising a magnetic material to identify a selected location of said internal structure, said element being capable of emitting a magnetic signal in response to an applied magnetic field, said system comprising:

a) a magnetic field generator for irradiating said element with an applied magnetic field, b) a movable magnetic field sensor for detecting said magnetic signal from a plurality of selected mutually displaced positions to produce a corresponding plurality of element-locating signals, and c) a computing apparatus for converting said signals to a location image of said internal structure.

25. A system as set forth in claim 24, where said applied magnetic field is spatially and temporally uniform.

26. A system as set forth in claim 24, said applied magnetic field being a low frequency ac magnetic field.

27. A system as set forth in claim 26, wherein said magnetic signal is non-linear in response to said low frequency ac magnetic field.

28. A system as set forth in claim 24, wherein said applied magnetic field is an ac field and said element comprises an amorphous magnetic material, said magnetic signal being characterized by Barkhausen jumps in response to an applied ac magnetic field.

29. A system as set forth in claim 28, wherein said element is elongated in form.

30. A system as set forth in claim 29, wherein said element is a length of wire comprising an amorphous magnetic material.

31. A system as set forth in claim 30, wherein said element is coated with absorbing material which absorbs therapeutic radiation and is pervious to magnetic fields.

32. A method as set forth in claim 29, wherein said element is spheroidal in form.

33. A system as set forth in claim 24, wherein said applied magnetic field is an ac field and said element comprises an amorphous magnetic material that is characterized by non-linear Barkhausen jumps in response to an applied ac magnetic field.

34. A system as set forth in claim 24, wherein said applied magnetic field is a dc field and said element comprises a ferromagnetic material.

35. A system as set forth in claim 24, wherein said location is a target for focussing thereon of therapeutic radiation.

36. A system for therapeutic treatment of an internal structure of a living body with therapeutic radiation after implantation, at said internal structure, of an element comprising a magnetic material to identify a selected location of said internal structure, said element being capable of emitting a magnetic signal in response to an applied magnetic field, said system comprising:

a) a magnetic field generator for irradiating said element with an applied magnetic field, b) a movable magnetic field sensor for detecting said magnetic signal from a plurality of selected mutually displaced positions to produce a corresponding plurality of element-locating signals, c) a computing apparatus for converting said signals to a location image of said internal structure, and d) a controlled source of therapeutic radiation for focussing a selected degree and duration of therapeutic radiation at a target determined from said location image of said internal structure.

37. A system as set forth in claim 36, where said applied magnetic field is spatially and temporally uniform.

38. A system as set forth in claim 36, said applied magnetic field being a low frequency ac magnetic field.

39. A system as set forth in claim 38, wherein said magnetic signal is non-linear in response to said low frequency ac magnetic field.

40. A system as set forth in claim 36, wherein said applied magnetic field is an ac field and said element comprises an amorphous magnetic material, said magnetic signal being characterized by Barkhausen jumps in response to an applied ac magnetic field.

41. A system as set forth in claim 40, wherein said element is elongated in form.

42. A system as set forth in claim 41, wherein said element is a length of wire comprising an amorphous magnetic material.

43. A system as set forth in claim 42, wherein said element is coated with absorbing material which absorbs therapeutic radiation and is pervious to magnetic fields.

44. A method as set forth in claim 41, wherein said element is spheroidal in form.

45. A system as set forth in claim 36, wherein said applied magnetic field is an ac field and said element comprises an amorphous magnetic material that is characterized by non-linear Barkhausen jumps in response to an applied ac magnetic field.

46. A system as set forth in claim 36, wherein said applied magnetic field is a dc field and said element comprises a ferromagnetic material.

47. A system as set forth in claim 36, wherein said location is a target for focussing thereon of therapeutic radiation.

* * * * *